US00PP11551P

United States Patent [19]

Mak

[11] Patent Number: Plant 11,551

[45] Date of Patent: Oct. 10, 2000

[54] ASIATIC HYBRID LILY PLANT NAMED 'CONQUISTADOR'

[76] Inventor: Johan A. Mak, 5595 Halls Ferry Rd., Independence, Oreg. 97351

[21] Appl. No.: 09/030,533

[22] Filed: Feb. 24, 1998

[51] Int. Cl.[7] ..... A01H 5/00

[52] U.S. Cl. ..... Plt./314

[58] Field of Search ..... Plt./313, 314

[56] References Cited

U.S. PATENT DOCUMENTS

P.P. 7,100 1/1990 Vletter ..... Plt./314

*Primary Examiner*—Howard J. Locker

[57] ABSTRACT

A new variety of a hybrid lily plant bearing semi-upright flowers of excellent form and long persistence, both on the plant and as cut-flowers. The flowers of the new plant are characterized by their red coloration, and by small, inconspicuous papillae surrounded by a small golden area encircled by red coloration at the base of each tepal. This combination is completely new in the Asiatic hybrid divisions of lilies suited to forcing and to mass commercial cultivation. The variety is highly resistant to botrytis disease and shows high tolerance to virus. The bulbs may be precooled and forced for cut-flower production.The clone is vigorous and is a good grower and propagator.

1 Drawing Sheet

BACKGROUND OF THE INVENTION

My new variety of lily plant originated as a seedling which first flowered in 't Zand, Netherlands, in 1989, The breeding efforts has as their objective the production of an Asiatic hybrid with large, unspotted or inconspicuously spotted red flowers, with flowers in upright position and with tall stems suited to forcing into flower out of season, such combination heretofore unknown in the lily breeding art.

I substantially achieved the desired objective by crossing Asiatic seedlings and cultivars selected for their intense red coloration with spots or with inconspicuous spotting, or known to be carrying the recessive gene for spotlessness, and also displaying tall stems suited to forcing for year-round use as cutflowers.

The flowers of my new lily are characterized by large size and broad-tepalled "bowl-shaped" form, unusually thick substance, and deep and intense red coloration with small, inconspicuous papillae confined to the basal third of each tepal, in an area parallel to the nectary furrows, extending about 1 cm from the apex of the nectary furrows and about 0.5 cm on each side of the basal tepal midrib. As the flower ages, the anthocyanin pigments in the area surrounding the papillae fade, revealing the golden to golden-orange carotene pigments in the underlying cell layers. This creates a golden "blaze" or blush on the basal third of each tepal. It possesses unusually strong, tall stems. In addition, the clone possesses to a high degree desirable characteristics of hybrid vigor. It forces rapidly and reliably year-round under greenhouse cultivation; in late winter to early spring in western Oregon, it typically flowers in 75 to 85 days from adequately precooled bulbs. The clone is a good grower and propagator, as observed at 't Zand, Netherlands, and at Salem, Oreg.

My new variety of lily plant has been asexually reproduced by me and under my direction at 't Zand, Netherlands, and at Salem, Oreg. Successive generations produced by natural propagation from bulblets, by bulb scale propagation, and by tissue culturing from bulb scale explants have demonstrated that the novel and distinctive characteristics of my new variety are fixed and hold true under asexual propagation from generation to generation.

DESCRIPTION OF THE DRAWING

My new variety of lily plant is illustrated in the accompanying photographic drawing, which shows the open bloom in full color and illustrates the flower form, the tepal arrangement and in particular the red coloration accented with a golden to golden-orange "blaze" or blush surrounding the small, inconspicuous papillae on the basal third of each tepal.

DESCRIPTION OF THE NEW VARIETY

The following is a detailed description of my new variety of Asiatic hybrid lily, with nomenclature according to the *International Lily Register* (Royal Horticultural Society of London, Second Edition, 1969), and with color designations according to the Color Chart of The Royal Horticultural Society, published by the Society in 1966.

The Plant

Origin: Seedling.

Seed parent: Selected unnamed red Seedling.

Pollen parent: Avignon (U.S. Plant Pat. No. 7,100).

Commercial classification: Hybrid Lilium clone.

Horticultural classification: Division 1-A, upright Asiatic hybrid lily, according to the Horticultural Classification of Lilies, Royal Horticultural Society of London.

Form: Single stem, erect and stately.

Height: 80 to 125 cm from bulbs 14 to 18 cm in circumference, provided their light levels are adequate; low light levels may cause "stretching."

Growth: Vigorous and upright.

Foliage quantity: Abundant.

Shape of leaf: Lanceolate (pointed); leaves in the upper third of the stem typically average 10–15 cm long and average 1.25 cm wide, with adequate nutrition.

*Texture*.—Leathery and glossy.

*Color*.—Dark green, lighter on lower side; color of upper leaf surface is typically R.H.S. C.C. Green 134 B to 139 B/C, depending upon light intensity, growing temperatures, and nitrogen levels in the growing media.

Bulb size: Any size, ranging to 25 cm circumference commercially.

Bulb color: White, with flushes of pink or yellow after exposure to light.

The Bud

Form: Obtuse, ovoid, and long.
Size: 8 to 11 cm long and 7 to 9 cm in circumference just prior to opening.
Color of apex of young bud: Greenish.
Color of bud: glossy red with light green midribs, which may be overlaid with red as well. Buds immediately prior to opening are typically R.H.S. C.C. Red 41 A/B adjacent to the midrib, shading to R.H.S. C.C. 32A Orange-Red at the tepal margin.
Opening: Bud opens slowly, in response to morning light, this takes about one hour.
Peduncle: Averages 10 to 14 cm, but it may elongate if light levels are too low or if bulbs have been improperly stored prior to forcing.

The Flower

Blooming habit: Annually in midseason, flowers once and profusely. It forces rapidly and reliably year-round under greenhouse cultivation from precooled bulbs.
Size: Flowers are medium large-sized, averaging 13 to 16 cm in diameter, the outer tepals are 2.5 to 3.50 cm wide, and the inner tepals are 4 to 5.5 cm wide.
Borne: In a single racemic inflorescence producing 10 to 15 flowers from a bulb 14 to 16 cm in circumference.
Shape: From a somewhat bowl shape by the second day after opening.
Tepalage: Typical of genus Lilium, with 6 imbricated tepals.
Tepal color: R.H.S. C.C. Red Group 44A, depending upon light levels and temperatures. Bright light and cool to moderate temperatures accentuate the red color; with extremely hot temperatures, it may lighten slightly to a more orange-red. As the flower ages, an area in the basal third of the tepals lightens to a golden to golden-orange color. The tepal undersurface is typically R.H.S. C.C. Red 41 A/B adjacent to the midrib, shading to R.H.S. C.C. 32A Orange-Red at the tepal margin.
Inner base of tepal: R.H.S. C.C. Orange Red Group 32A in the area parallel to the nectary furrows, extending 1 cm. beyond their apex and extending laterally 0.5 cm. on each side of the basal tepal midrib; this is the area that encircles the small, inconspicuous papillae.
Tepal spotting: At the main part of the base, color is R.H.S. C.C. Greyed Purple 183A. Papillae are small and inconspicuous, confined to the basal third of each tepal. There are typically 25–40 papillae on each inner tepal and 15–25 papillae on each outer tepal.
Tepal longevity: Tepals stay on stems about three weeks.
Pedicel length: Average 7 to 12 cm long.
Pedicel color: Dark green with plum overlay.
Pedicel form: Sturdy and ascending.
Apperance: Flower is shiny.
Disease resistance: The flower and plant are resistant to disease; in particular, they are resistant to viruses and Botrytis blight.
Fragrance: None.
Lasting quality: The flower is long lasting, both on the plant and as a cut-flower.

The Reproductive Organs

Stamens: Arrangement typical of genus Lilium. Six stamens with soft green to palest pink filaments 5 to 7 cm long.
Pollen and anthers (dehisced): R.H.S. C.C. Greyed Orange Group 166A.
Pistil: One in number, 7 to 9 cm long.
Stigma: R.H.S. C.C. Red Group 181A.
Characteristics of ovary: Characteristic of genus Lilium.

The Fruit

Fertility: The fruit bears fertile seed.
Shape: Ovoid.
Color at maturity: Soft brown, sometimes overlaid with soft plum.

I claim:

1. A new and distinctive variety of Asiatic hybrid lily plant substantially as herein shown and described, characteristics by its high resistance to disease; its tolerance of virus and botrytis blight; its vigorous growth and rapid natural propagation, the excellence of its flower form, size, and substance; its versatility both as a garden plant and as a cut-flower producer from pre-cooled bulbs forced under glass out of season; and in particular by its red flower coloration with small, inconspicuous papillae encircled by an area in which the anthocyanins fade as the flower ages to produce a golden to golden-orange "blaze" or blush on the basal third of each tepal, a combination unique among Asiatic hybrid lilies suited to forcing and to mass commercial cultivation.

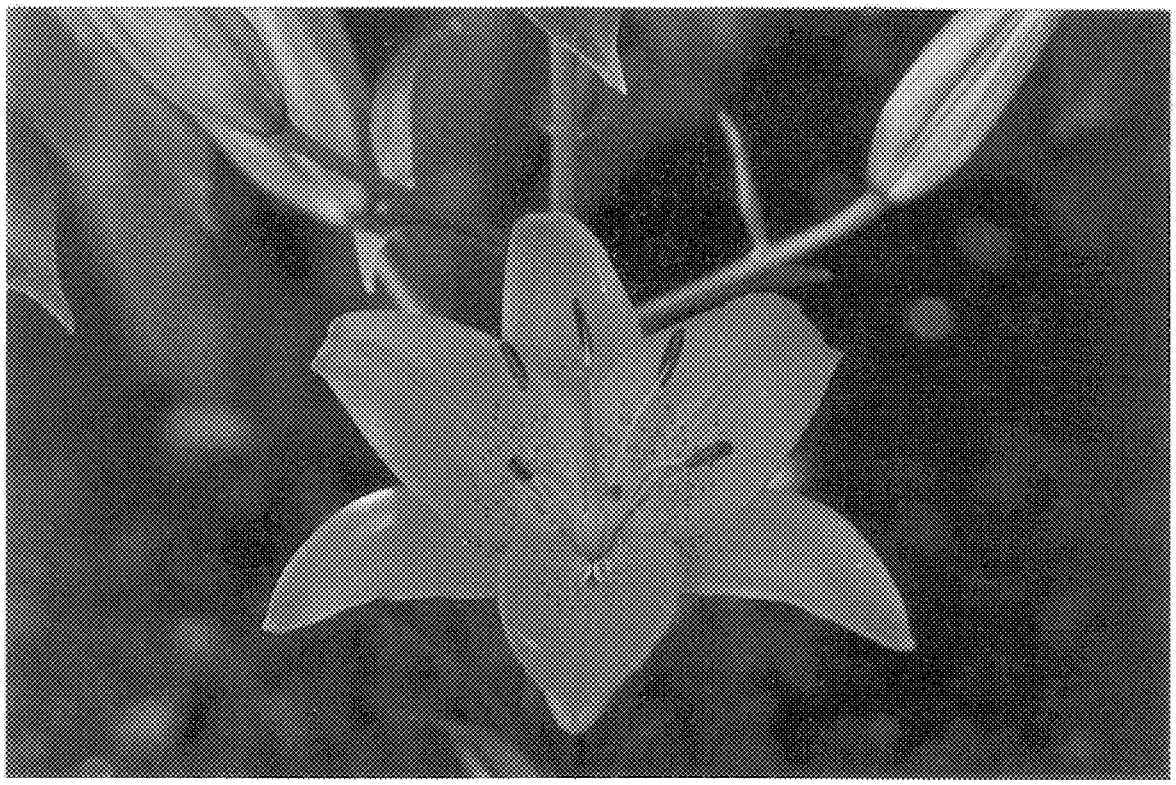

* * * * *